United States Patent [19]

Kim

[11] 4,323,562

[45] Apr. 6, 1982

[54] ADJUVANT FOR STIMULATING PRODUCTION OF LYMPHOCYTES

[76] Inventor: Dae-Eun Kim, 545-90, 6-dong, Anyang City, Kyonggi-do, Rep. of Korea

[21] Appl. No.: 169,324

[22] Filed: Jul. 16, 1980

[30] Foreign Application Priority Data

Jul. 27, 1979 [KR] Rep. of Korea .......................... 2546

[51] Int. Cl.³ ............................................. A61K 35/78
[52] U.S. Cl. .................................................... 424/195
[58] Field of Search ......................................... 424/195

[56] References Cited

PUBLICATIONS

Cancer Research, vol. 26, Jun. 1966, pp. 597, 598 & p. 719 (Cancer Chemotherapy Screening Data XLV).

Primary Examiner—Donald B. Moyer
Attorney, Agent, or Firm—Blanchard, Flynn, Thiel, Boutell & Tanis

[57] ABSTRACT

This invention relates to an adjuvant effective for stimulating the production of lymphocytes in the circulating blood of a mammal, which adjuvant is an extract from Atractylis lyrata s. et z.

1 Claim, No Drawings

ADJUVANT FOR STIMULATING PRODUCTION OF LYMPHOCYTES

DESCRIPTION OF THE INVENTION

This invention relates to an extract of Rhizoma of Atractylis lyrata s. et z., a perennial herb, which belongs to the family Compositae and grows in fields and mountains, and which is used as a digestive aid and a diuretic in herbal medicine. By many experiments, according to the present invention, it was proved that the extract promoted immunological surveillance by stimulating lymphatic systems in vivo when it was administered to animals and it acts as an immuno-therapeutic agent for antitumor therapy.

This adjuvant is most effective when it is administered with optimal dosage and optimal concentration, like many other mitogenic chemicals. When the extract is added to the drinking water of test mice in an optimal dose, 40% of the test mice recovered from intraperitoneal inoculation of Sarcoma 180.

Atractyl (mandelic acid isoamyl ester) and other derivatives of mandelic acid, which are characterized by a local stimulating effect, proved to be somewhat effective for treating mice inoculated with Sarcoma 180. However, the effects were significantly less than that of the extract of the natural herb.

The main compositions of Rhizoma Atractylis known hitherto are 1.5% steam distillate thereof. Atractylon, the chief component of the steam distillate, has a characteristic aroma.

The Rhizoma Atractylis utilized for this invention is native Rhizoma Atractylis, Rhizoma Atractylis alba and dried Atractylis without the outer shell of the Rhizoma. Rhizoma Atractylis alba can be administered as a powder. This material can also be administered as a tea. A dose of the extract could also be administered as a water emulsion, a tablet or gelatin capsules, etc.

EXAMPLE 1

A lady (age: 67 years) diagnosed as having an inoperable cancer drank tea made of Rhizoma Atractylis for six months. Remission of the cancer was observed.

To make the tea, 100 grams of dried Rhizoma Atractylis was put in a traditional Korean clayware used for preparing herbal tea with 1 liter of tap water and was boiled for two hours under mild heat. During the tea-making process, the pot was covered with a sheet of Korean traditional native paper.

After remission occurred, the patient received by oral administration, 3 grams of powder of Rhizoma Atractylis alba daily for over three years to prevent metastasis. Since then no metastasis has occurred for another seven years.

EXAMPLE 2

Nasal polyps of a ten month old female dog disappeared completely after 0.1 grams/kg/day of powder of Rhizoma Atractylis alba was administered for 10 days. The daily dose was divided into many small dosage amounts and was administered orally to the dog several times daily without water.

EXAMPLE 3

The cytotoxicity of a water extract of Rhizoma Atractylis was tested on chicken embryo fibroblast cells cultured in Hank's balanced salt solution. No cytotoxicity was observed at all, even when the undiluted original extract was used. The water extract was prepared by slicing dried Rhizoma Atractylis, heating it with distilled water at 100° C. for 30 minutes to make a 10% solution, and then diluting that solution with water to a concentration of 1/32 the concentration of the original extract by the two fold dilution method. The diluted extract was added so as to be ten weight percent of the culture medium when it was cultured.

EXAMPLE 4

Experimental animals:
White male mice (I.C.R.) weighing 16 to 18 g.
Extraction:
200 grams of dried and sliced Rhizoma Atractylis alba and about 800 ml of distilled water were put in a 2 liter flask to which was attached a reflux condenser. The mixture was boiled with an electric heater for 30 minutes. The liquid was then filtered while it was warm. New water was added and the same procedure was repeated twice more. The filtrates were combined, evaporated on a water bath and then with a drying oven. A powder in an amount of 34.5 weight % of the starting material was obtained.
Administration to experimental animals:
1 gm of the dried powder was dissolved in 160 ml of tap water and was put into the animal cages in place of the usual drinking water, so that the test mice ingested it ad libitum. 2 to 4 ml of the solution was taken per day by each mouse.
Testing and Results:
By differential count of white blood cells, an extraordinary increase in lymphocytes was observed caused by three week's drinking of the test liquid. Some prolongation of the survival time against intraperitoneal inoculation of Sarcoma 180 was observed, after the liquid was ingested for a month.

EXAMPLE 5

0.18% of fat-soluble material was extracted from 1 gm of the powder of Example 4 with diethyl ether using a Soxhlet's extractor. Three portions, namely, an ether-soluble portion, the remaining solid portion and a mixture of both of them, were obtained and were tested on I.C.R. mice in the same way as in Example 5.

The results showed that the ether extract was the most effective portion for elevating the lymphocytes and resisting the effect of Sarcoma 180. On the other hand, the remaining (ether-nonsoluble) portion imparts a tonic effect for male mice. Both fractions kill the other's effect when they are combined together.

EXAMPLE 6

A large volume of ether extract from a powder of Rhizoma Atractylis alba was produced. Some definite weights of the ether extract were dissolved in small volumes of ethanol, and then diluted with water to obtain emulsions of ether extract/water of 1 mg/100 ml, 2 mg/100 ml, 3 mg/100 ml, 4 mg/100 ml and 5 mg/100 ml.

The emulsions were administered to I.C.R. male mice for one month as described in Example 4, and then the mice were inoculated with 200,000 cells of Sarcoma 180 intraperitoneally. The survival time of the inoculated mice was regressed to the concentration of ether extract administered. The coefficient of regression, $B_{yx}=0.63$, shows that when 1 mg of ether extract is administered in 100 ml of drinking water, the survival time of the mice is prolonged by 0.63 days, on the average.

EXAMPLE 7

An unsaponified extract was prepared at low temperature (70°–80° C.) from the ether extract, and was made into emulsions by mixing with water as described in Example 6, to obtain emulsions containing amounts of the unsaponificate obtained from the ether extract. Expressed in terms of the weight of ether extract used to prepare the unsaponificate extract to the amount of water used to make the emulsions, the emulsions contained 1 mg/100 ml, 2 mg/100 ml, 3 mg/100 ml and 4 mg/100 ml.

The emulsions were administered to I.C.R. mice as described in Example 4 for one month, and then the mice were inoculated with 200,000 cells of Sarcoma 180 intraperitoneally. The survival time of inoculated mice was regressed to the concentrations of unsaponificate. The coefficient of regression, $B_{yx}=0.92$, shows that when the unsaponificate extract contained in 1 mg of the ether extract is diluted in 100 ml of drinking water and is administered to mice, the survival time of the mice is prolonged 0.92 days.

EXAMPLE 8

Screen test for high dose responses
Material: pulvis Rhizoma Atractylis alba
Fractions:
  E = Ether extract
  U = Unsaponificate
  A, P = Two fractions in U fraction obtained by chromatography using specially prepared organic solvent.

Each fraction was diluted to 5 steps by two fold dilution method.
  E 5 = 5 mg E/100 ml
  E 10 = 10 mg E/100 ml
  E 20 = 20 mg E/100 ml
  E 40 = 40 mg E/100 ml
  E 80 = 80 mg E/100 ml
  U 5 = U in 5 mg E/100 ml
  U 10 = U in 10 mg E/100 ml
  U 20 = U in 20 mg E/100 ml
  U 40 = U in 40 mg E/100 ml
  U 80 = U in 80 mg E/100 ml
  A 5 = A in 5 mg E/100 ml
  A 10 = A in 10 mg E/100 ml
  A 20 = A in 20 mg E/100 ml
  A 40 = A in 40 mg E/100 ml
  A 80 = A in 80 mg E/100 ml
  P 5 = P in 5 mg E/100 ml
  P 10 = P in 10 mg E/100 ml
  P 20 = P in 20 mg E/100 ml
  P 40 = P in 40 mg E/100 ml
  P 80 = P in 80 mg E/100 ml
Experimental design:

Seven I.C.R. male mice weighing 16–18 g were put into each cage and one cage was considered to be one block. 21 blocks were provided. The respective twenty testing fractions were each administered to one of the blocks in place of the usual drinking water. To the control block ordinary tap water was given for drinking.

Test 1:
To examine the effect of continuous intake of the dilutions of the fractions for a long time on the growth rates of the test animals, the body weight was measured at the beginning of the test and then four times weekly and these measured values were compared to those of the control animals.

Test 2:
To establish the pharmacological action, differential count of white blood cells was made from each mouse's blood smear at 3 weeks after the start of the testing period, which is considered to be the time when the lymphocyte level begins to be raised.

Test 3:
To compare the therapeutic effects of each block, 5 mice in each block were inoculated with 180,000 cells of Sarcoma 180 intraperitoneally and the mice were observed for 40 days after inoculation.

Test 4:
The two mice in each block which were not inoculated were sacrificed after 3 months from the beginning of the experiment and autopsy was performed.

Results from Test 1—The growth rate of a mouse is the rate of increased body weight when the body weight from the first measure is considered to be 1. Statistically, this was calculated by randomized complete block design.

| Block | Analysis of Variation | | | |
|---|---|---|---|---|
| | D.F. | S.S. | M.S. | F |
| Total | 104 | 16.9605 | — | |
| Replication | 4 | 14.1850 | — | |
| Block | 20 | 1.9078 | 0.0953 | 8.83** |
| Error | 80 | 0.8677 | 0.0108 | |

**$n_1 = 4$  $n_2 = 80$  $F_{0.05} = 2.48$  $f_{0.01} = 3.56$ $\overline{Sd} = \sqrt{2 \times 0.0108/5} = \sqrt{0.043} = 0.2073$ L.S.D. $= t_{0.05}$ (d.f. $= 80$) $\times \overline{Sd} = 1.99 \times 0.2073 = 0.4125$ When each block was compared with the control block according to L.S.D., there was no significant differences of the growth rates of the test animals compared with those of the control mice.

Results from Test 2—All the testing blocks exhibited a rise of the lymphocyte count and the highest was that of U 20 (81.0±2.23%). There could be found many immature forms and buddings of lymphocyte providing indirect proof of the continuous stimulation of the lymphatic system.

Results from Test 3:

| | Number of disease-free mice at 40th day after inoculation | | | |
|---|---|---|---|---|
| | Fraction | | | |
| Dilution | E | U | A | P |
| 5 | — | — | — | — |
| 10 | — | — | 1 | — |
| 20 | 1 | 1 | 2 | — |
| 40 | — | — | — | 1 |
| 80 | 1 | — | — | 1 |

Result from Test 4:
The thickness of the wall of digestive tract was observed.

EXAMPLE 9

20 mg of fraction A/ml of acetone and 43 mg of fraction P/ml of acetone were tested for the phytohemagglutinin stimulation test and migration inhibition test at Catholic Medical Center, by employing a concentration of 20 weight % of the culture media. No mitogenic effect in vitro was observed.

EXAMPLE 10

A healthy female (age: 47 years, the inventor) ingested 1 gm of powder of Rhizoma Atractylis alba after each meal for four weeks and was tested liver function at Medical College of Seoul National University every two weeks. The results are shown in Table 1.

TABLE 1

| Time | Total Protein | Albumin | Total Bilirubin | Glucose | SGOT | Cholesterol |
|---|---|---|---|---|---|---|
| before administration | 7.4 | 4.6 | 0.33 | 92 | 36 | 155 |
| 2 weeks | 7.65 | 4.8 | 0.46 | 88 | 42 | 159 |
| 4 weeks | 7.4 | 4.64 | 0.4 | 122 | 26 | 140 |

| Time | BUN | Creatinine | Inorg. P. | $Ca^{++}$ | Alk. phase | LDH |
|---|---|---|---|---|---|---|
| before administration | 17 | — | — | — | 96 | 292 |
| 2 weeks | 14 | 1.0 | 4.5 | 9.2 | 101 | — |
| 4 weeks | 12 | 0.9 | 3.7 | 9.1 | 92 | — |

EXAMPLE 11

Mandelic acid, mandelic acid isoamyl ester (Atractyl), mandelic acid methyl ester, mandelic acid ethyl ester and atrolactic acid were tested by the same procedure as described in Example 6. They were observed to be somewhat effective against intraperitoneal inoculation of Sarcoma 180 in mice. However, they were less effective than the extract from the natural herb. The optimal dose to cure the mice completely could not be established.

The embodiments of the invention in which an exclusive property or privilege is claimed are defined as follows:

1. A method for stimulating the production of lymphocytes in the circulating blood of a mammal, which comprises:
administering to the mammal an adjuvant in an amount effective to stimulate the lymphatic system to elevate the number of lymphocytes in the blood, said adjuvant being a water-soluble, diethyl ether-soluble, unsaponified, fraction of Atractylis lyrata s. et z.

* * * * *